US00PP12554P2

(12) United States Plant Patent
Rother

(10) Patent No.: US PP12,554 P2
(45) Date of Patent: Apr. 16, 2002

(54) AGAPANTHUS PLANT NAMED 'SNOWSTORM'

(75) Inventor: Reinhard W. Rother, Emerald (AU)

(73) Assignee: Stephen J. M. Wilken, Silvan Victoria (AU)

( * ) Notice: Subject to any disclaimer, the term of this patent is extended or adjusted under 35 U.S.C. 154(b) by 0 days.

(21) Appl. No.: 09/207,149

(22) Filed: Dec. 8, 1998

(51) Int. Cl.[7] ..... A01H 5/00
(52) U.S. Cl. ..... Plt./263
(58) Field of Search ..... Plt./263

(56) References Cited

PUBLICATIONS

Copy of Australian Plant Breeder's Rights Application form (Feb. 2, 1989).
Copy of New Zealand Plant Variety Rights Application form (Jun. 14, 1995).
Copy of New Zealand Grant Certificate (Mar. 25, 1997).

UPOV–ROM GTITM Computer Database 1999/02, GTI JOUVE Retrieval Software, citations for 'Snowstorm', May 1999.*

Huxley, A., Griffiths, M., and Levy, M. The New Royal Horticultural Society Dictionary of Gardening. vol. 1 p. 80, Jul. 1992.*

* cited by examiner

*Primary Examiner*—Bruce R. Campell
*Assistant Examiner*—Michelle Kizilkaya
(74) *Attorney, Agent, or Firm*—Foley & Lardner

(57) ABSTRACT

A new and distinct cultivar of agapanthus named 'Snowstorm' having a higher number of umbels per inflorescence, dense foliage of very short narrow leaves compared with other cultivars of the same genus *Agapanthus praecox orientalis* 'Albus'.

2 Drawing Sheets

FIELD OF THE INVENTION

This invention relates to a new and distinct cultivar of agapanthus, botanically known as *Agapanthus praecox* ssp. *orientalis,* and referred to by the cultivar name 'Snowstorm'.

DESCRIPTION OF INVENTION

The new cultivar was discovered by the inventor in Emerald, Victoria, Australia and resulted from the open pollination of *Agapanthus praecox* ssp. *orientalis* 'albus' in Autumn 1982. The new cultivar was selected from the progeny by the inventor in Emerald, Victoria, Australia with the selection being primarily due to the following criteria: uniform plant height, flower number, size of open flower head, flower color and evergreen characteristics.

Following the open pollination of agapanthus 'albus' (unpatented) referred to above, seed was collected and germinated following typical nursery conditions, and the individual plants planted into assessment beds in the nursery located in Emerald, Victoria, Australia. The plants were assessed in-ground, when they were divided for container-growing trials and uniformity assessment. Using the above selection criteria, asexual propagation of the plant by division was performed vegetatively through many generations.

The new cultivar 'Snowstorm' is evergreen, dwarf, white-flowered and heavy flowering, and is primarily distinguished from its seed parent and from other cultivars of the genus such as Agapanthus 'Snowdrops' (unpatented) and Agapanthus 'Snowball' (unpatented), which are the closest comparators known to the inventor, by the high number of florets per inflorescence and by being reliably evergreen. In addition, the new cultivar has dense foliage compared to the medium density foliage of the other agapanthus cultivars, the leaves of the new cultivar being very short and narrow compared with other cultivars.

The accompanying color photographs show the high flower density and leaf characteristics as closely as possible with illustrations of this type.

The photograph on sheet one shows a mature plant exhibiting the high flower density and leaf characteristics.

The photograph on sheet two is a closeup view of a typical flower head and leaf of the new cultivar and a similar view of the flower head and leaf of the comparator 'Snowdrops'.

In the following description color references are made to The Royal Horticultural Society Colour Charts. The color values were determined on plant material grown in ambient outdoor conditions at Emerald, Victoria, Australia.

Plant

Type: Clump forming perennial.

Height: Medium height — 70–75 cm (relatively short compared to the other cultivars).

Growth habit and rate: Upright growth habit; medium in size; plants will normally flower in the first 12 months after they have been divided. The flowering period is late Spring to mid-Summer.

Roots: Fleshy, thick, with some aerial roots typical of the sub-species *praecox orientalis.*

Leaves: Foliage dense, very short (<40 cm), narrow (<20 mm), mid-green to yellow-green in color (RHS 144A), medium to many leaves per fan (6–12).

*Leaf margin.*—Smooth.

*Leaf texture.*—Smooth.

*Leaf venation.*—Present, runs lineally with the midrib apparent on the rear.

*Leaf arrangement.*—Radical.

*Leaf shape.*—Lorate with acute tip.

*Leaf aspect.*—Erect in the center of clump, arching in periphery.

*Leaf density.*—More dense than is typical for this genus.

Inflorescence

Medium to many florets (approx. 60) shape flat round, above foliage. The flower has a medium pedicel (approx. 40 mm), erect, perianth short (<40 mm), diameter medium (approx. 33 mm), shape narrow campanulate, length of perianth lobe in relation to perianth tube longer, perianth color inner white (RHS 155A to 155B), outer white (155A to 155b), timing early to medium (spring/summer), medium to long flowering.

The new cultivar is described as being hardy and has not shown any abnormal susceptibility to diseases or insects most commonly encountered in the cultivation of this species. As will be evidenced from the photograph of sheet 2, 'Snowstorm' is an evergreen, medium growing (70–75 cm) Agapanthus with dense foliage, whereas 'Snowdrops' has medium density foliage color. The leaves are very short (<40 mm), and narrow, whereas 'Snowdrops' has a slightly wider leaf width. It has many leaves (6–12) per fan, mid green to yellow green (RHS 141B). Inflorescence number is high (approx 60), whereas 'Snowdrops' has a medium number of florets per inflorescence (approx 50). The florets have a flat round shape and 'Snowdrops' has narrow flat round shape and are situated above the foliage. The peduncle is green, RHS 143B, and has an average length of 520 mm. The flower pedicel is medium (approx 40 mm), erect, green, RHS 143B, with a short perianth that has a medium diameter (approx 33 mm). The peduncles have an average length of 520 mm within a range of 480–600 mm +/−45 mm. Flower shape is narrow campanulate and it has a longer perianth lobe in relation to the perianth tube. The number of umbels per plant will vary according to the age of the plant with a younger plant having less umbels. Average of 25 blooms on a three-year-old plant, 50 blooms on a four-year-old plant and up to 100 blooms on a five-year-old plant. The flower color for both the inner and outer side is white (RHS 155AB). It is an early to medium flowerer usually flowering in spring and summer, and flowering for a medium to long period. Flowers are 6-petalled, with individual petals joining at the corolla. Petals have undulate margins, pronounced midribs and acute tips. Seeds are present in the black seed capsule some time after flowering has finished. Lateral buds will typically open first but are not always spent by the time the inner/upper buds are open. Flowers are typically 34–42 mm in size and are tubular to campanulate with corona absent. The bloom is not significantly fragrant. Spathe valves are deciduous. There are 6 stamens and the ovary is superior. The color is RHS 155 A to 155 B. Anthers are RHS 155 C.

As described above the new cultivar has dense foliage with the leaves being very short and narrow and a high number of florets per inflorescence with the flower color being uniformly white.

I claim:

1. A new and distinct agapanthus plant named 'Snowstorm', as illustrated and described.

* * * * *

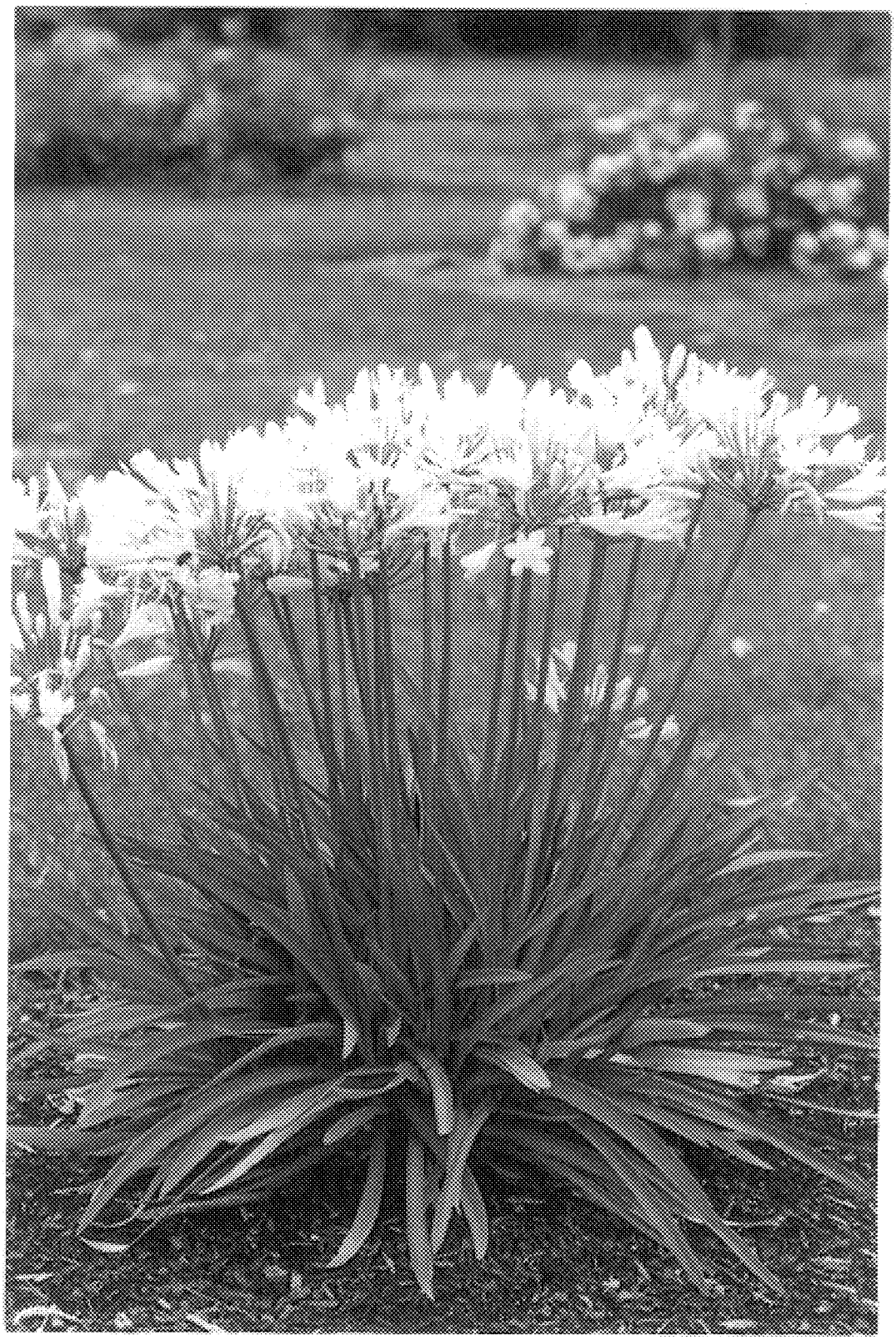

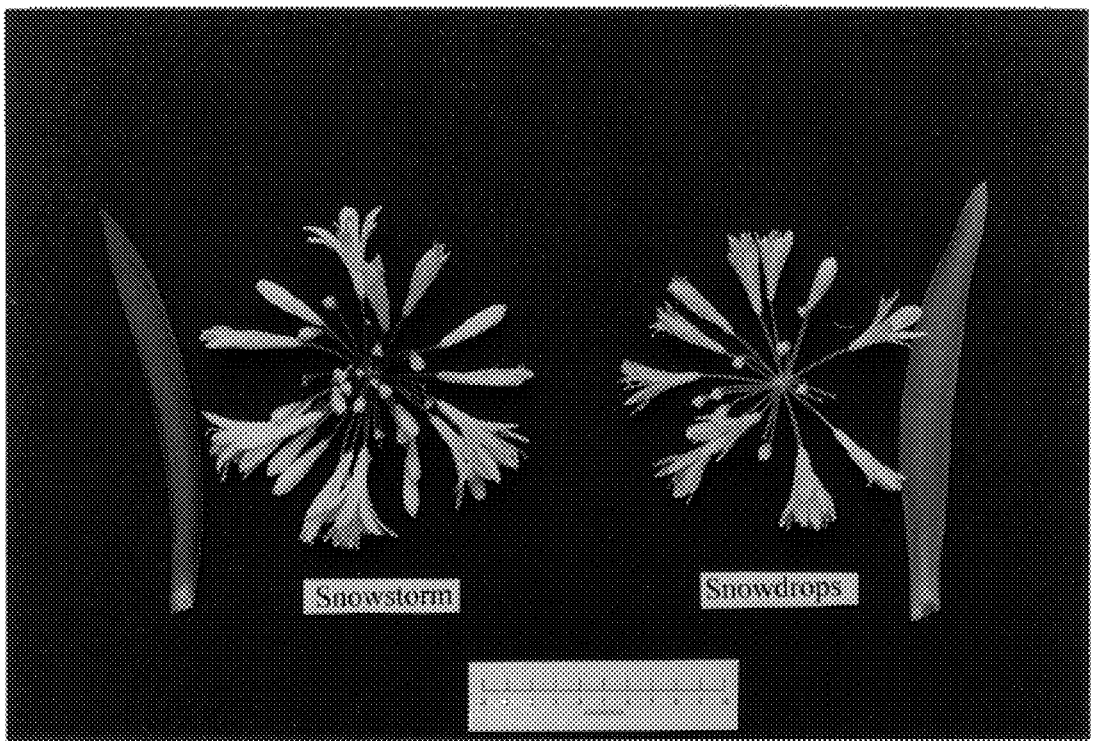
Snowstorm
Snowdrops